United States Patent [19]
Lee

[11] Patent Number: 5,101,836
[45] Date of Patent: Apr. 7, 1992

[54] FLEXIBLE LOW PROFILE MICROWAVE ARRAY FOR HYPERTHERMIA OF SUPERFICIALLY LOCATED TUMORS

[75] Inventor: Eric R. Lee, San Mateo, Calif.

[73] Assignee: The Board of Trustees of the Leland Stanford Junior University, Stanford, Calif.

[21] Appl. No.: 485,989

[22] Filed: Feb. 27, 1990

[51] Int. Cl.⁵ .............................................. A61N 5/02
[52] U.S. Cl. ....................................... 128/804; 128/400
[58] Field of Search ............... 128/783, 798, 804, 395, 128/400, 402; 600/9, 10, 13, 14, 15

[56] References Cited

U.S. PATENT DOCUMENTS

| | | | |
|---|---|---|---|
| 4,140,130 | 2/1979 | Storm, III | 128/804 X |
| 4,197,851 | 4/1980 | Fellus | 128/798 X |
| 4,397,313 | 8/1983 | Vaguine | 128/804 X |
| 4,974,587 | 12/1990 | Turner et al. | 128/804 X |

FOREIGN PATENT DOCUMENTS

| | | | |
|---|---|---|---|
| 1910972 | 10/1969 | Fed. Rep. of Germany | 128/783 |
| 3320990 | 12/1984 | Fed. Rep. of Germany | 128/804 |
| 2135891 | 9/1984 | United Kingdom | 128/804 |

*Primary Examiner*—Lee S. Cohen
*Attorney, Agent, or Firm*—Henry K. Woodward

[57] ABSTRACT

A low profile flexible microwave radiating array includes a base structure on which are positioned a plurality of rigid platforms which support individual antenna elements. In one embodiment the support platforms are generally cubical in configuration with the antennas being fabricated as microstrip radiators which are bonded to one surface of the cube. A coaxial connector is provided to energize the antenna. The rigid platforms maintain the desired spacing and orientation between the antenna and the skin of a patient, and the individual platforms and the flexible base permit the blanket to conform with complex surfaces on a patient.

15 Claims, 2 Drawing Sheets

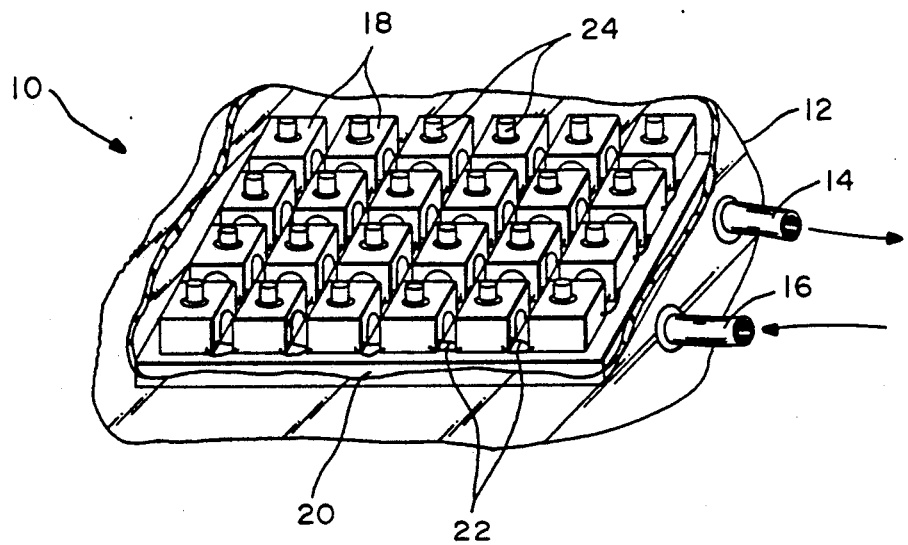
FIG.—1
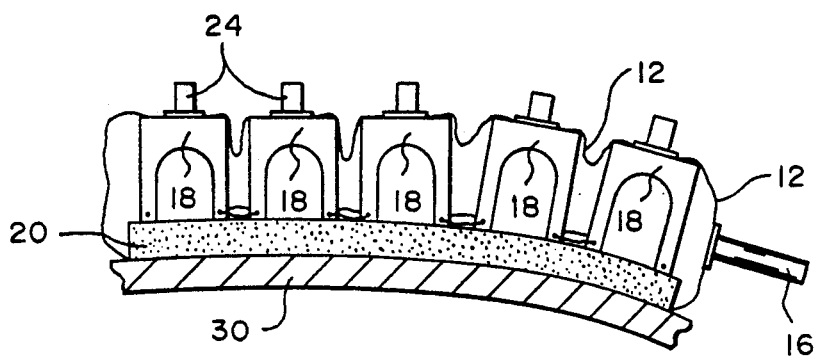
FIG.—2
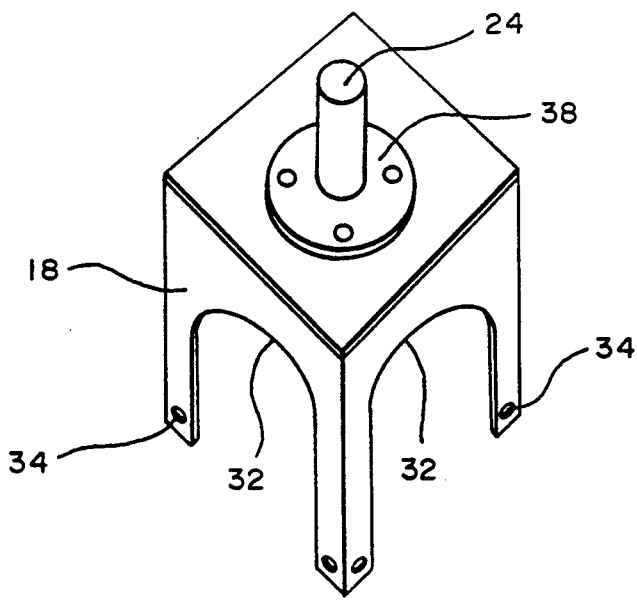
FIG.—3

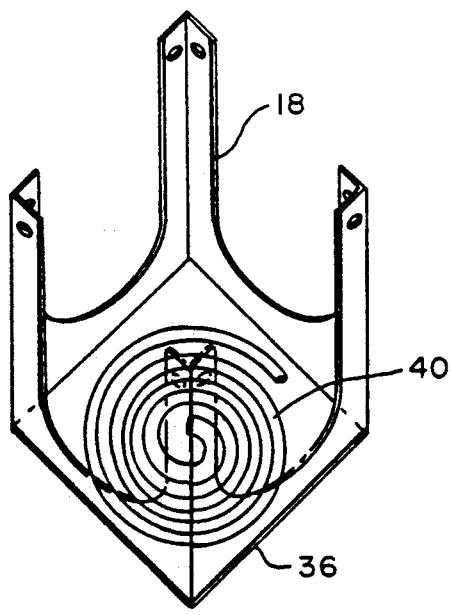
FIG.—4
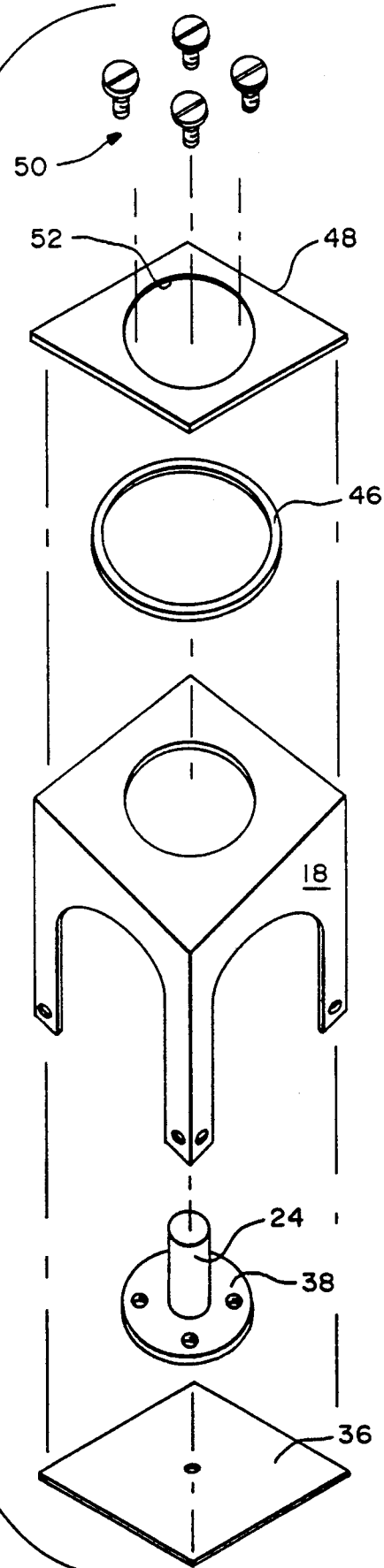
FIG.—5

5,101,836

FLEXIBLE LOW PROFILE MICROWAVE ARRAY FOR HYPERTHERMIA OF SUPERFICIALLY LOCATED TUMORS

The U.S. Government has rights in the disclosed invention pursuant to NIH Contracts No. CA 40434 and No. CA 44665 with Stanford University.

BACKGROUND OF THE INVENTION

This invention relates generally to hyperthermic treatment of superficially located tumors, and more particularly the invention relates to a flexible microwave array which can conform to complex curvatures of the human body for uniform electromagnetic heating of such tumors.

The use of microwave applicators for hyperthermia treatment of superficial tumors is well known. However, difficulties have been encountered in applying such devices over large areas with complex curvatures, such as in the neck and chest area of patients, while retaining the antenna(s) in an evenly spaced perpendicular alignment with the surface with proper inter antenna spacings in order to facilitate uniform heat treatments.

The present invention permits mechanical mounting and electromagnetically coupling arrays of microwave radiating antenna for the treatment of human carcinomas such that the energy deposited on the diseased tissue can remain generally constant and uniform despite having to curve over the complex contours of the human body.

SUMMARY OF THE INVENTION

Accordingly, an object of the invention is an improved hyperthermia apparatus for treating superficial tumors.

Another object of the invention is a microwave array structure which readily conforms to complex curvatures while facilitating a uniform hyperthermia treatment.

Still another object of the invention is a mounting structure for antennas which allows the fields of adjacent antennas to smoothly combine, maintains a desired spacing between antennas and treated surface, yet allows mounting of the antennas on a curved surface.

A feature of the invention is the use of semirigid mounting platforms with cutout sections between adjacent antenna mounts on which microwave antennas are mounted.

Another feature of the invention is an electromagnetically transparent water permeable, flexible base on which the mounting platforms are supported.

Briefly, in accordance with a preferred embodiment of the invention, a plurality of microstrip antennas are fabricated in which each antenna is formed on a side of a printed circuit board while a ground plane is provided on the opposing surface. Each antenna is mounted on a rigid platform which can be a cubicle in configuration. The platforms are arranged in an array on a flexible base with the antennas uniformly spaced from the base. Each platform is flexibly attached to adjacent platforms near the base to maintain alignment of the antennas but allowing flexing of the orientation of an antenna relative to an adjacent antenna. The antennas are encased in a sealed flexible housing such as plastic whereby the base and platforms can be maintained in a water environment. An RF coupler is provided on each platform for energizing the antenna. Variable sizes of arrays can be readily provided with the antennas varied in size for particular operating frequencies. The rigid platforms maintain the desired spacing and antenna alignment for optimum hyperthermia treatment yet permit variable orientations of the antennas relative to each other and relative to the mounting surface.

The invention and objects and features thereof will be more readily apparent from the following detailed description and appended claims when taken with the drawing.

BRIEF DESCRIPTION OF THE DRAWING

FIG. 1 is a perspective view of a flexible microwave blanket in accordance with one embodiment of the invention.

FIG. 2 is a side view illustrating the conforming placement of the blanket of FIG. 1 on a curved surface.

FIG. 3 is a perspective top view of an antenna support platform in the embodiment of FIG. 1.

FIG. 4 is a perspective bottom view of the antenna support platform of FIG. 3 illustrating its use with a microstrip spiral antenna.

FIG. 5 is an exploded perspective view of the antenna platform of FIGS. 3 and 4.

DETAILED DESCRIPTION OF ILLUSTRATIVE EMBODIMENTS

Referring now to the drawing, FIG. 1 is a perspective view of a flexible microwave array in accordance with one embodiment of the invention as illustrated generally at 10. The structure includes a fluid retaining housing 12 which is shown partially in section to facilitate the view. Preferably, the housing 12 is comprised of transparent sheet vinyl. Two hoses 14 and 16 extend through the housing for the flow of the water coolant such as deionized degassed water.

A plurality of rigid support structures 18 are arranged in rows and columns on a pervious support base 20 which may comprise a reticulated filter foam material. Each of the support structures 18 comprises a cube in which one surface is removed. The open surface is positioned on the base 20 and can be glued in place to maintain its position thereon. Each cube is fastened to an adjacent cube at their bases such as by nylon string shown at 22 to maintain the alignment of the rows and columns of the array. The top surface of each cube supports a coaxial connector 24 for the reception of RF energy.

In accordance with one feature of the invention, the array of support structures can flex two dimensionally in order to conform with complex surfaces of the human body during the treatment of superficially located tumors. FIG. 2 is a side view of the structure illustrating the conforming of the support structures on an curved surface 30. It will be noted that he cubes 18 are free to align perpendicular to the surface as indicated by the center lines of the cubes. It will be appreciated that the array is free to flex in a second dimension also for two-dimensional positioning of the blanket on a patient. The spacing of the cubes is exaggerated in the figure, actual spacing is on the order of 1.5 mm.

FIG. 3 and FIG. 4 are a perspective top view and a perspective bottom view, respectively, of a cube 18. The sides of the cube are preferably made of a transparent plastic polycarbonate sheet such as Lexan ® supplied by General Electrical Company. Portions of the side surfaces adjacent to other cubes are removed as shown at 32 to allow the fields of adjacent antennas to smoothly combine and facilitate the flow of fluid within the cube. Holes 34 are provided at corners of the base of a cube to facilitate the attachment of adjacent corners of cubes by thread as illustrated at 22 in FIG. 1.

Mounted to the inside of the top surface of the cube opposite from the coaxial connector 24 is a printed circuit board. As illustrated in FIG. 4, one surface of the printed circuit board 36 has a spiral antenna 48 formed thereon by conventional photoresist masking and etching techniques. The radiating surface of the antenna facing the water has a plastic film bonded to it which isolates the antenna electrically from the coupling water and acts as a final electromagnetic impedance matcher. The opposite surface of the printed circuit board is a copper ground plane and abuts the top surface of cube 18 and can be fastened in place by glue or nonconductive string. A hole is formed in the top surface of the cube 18 whereby the flange 38 of the coaxial connector 24 engages the ground plane surface of the printed circuit board and can be soldered thereto. The center conductor of the coaxial connector 24 extends through the printed circuit board and electrically contacts the inner end of the spiral antenna 40.

FIG. 5 is an exploded perspective view of the antenna and support platform. Printed circuit board 36 has a hole in the center to receive the inner conductor of the coaxial cable which is in electrical contact with the spiral antenna 40. The printed circuit board 36 rests against and is supported by the top surface of cube 18. The top surface has a hole 42 therein to permit the flange 38 of the coaxial connector 24 to rest on the copper ground plane of the printed circuit board 36. The plastic sheet housing 12 must have holes therein to allow the coaxial conductors 24 to extend outside of the housing. To prevent leakage of fluid through the hole in the housing, an o-ring 46 is placed between the plastic sheet and the top surface of support 18, and a plate 48 is then fastened to the flange 38 of the coaxial conductor by means of screws 50 whereby the o-ring is maintained in pressure engagement between the plate 48 and the top surface of the support 18 and the vinyl sheet of the housing 12. The plate 48 has a hole 52 centrally located therein which allows the projection of the coaxial connector 24 therethrough. The screws 50 which engage threaded holes in the flange 38 of the coaxial connector of 24 abut the hole 52 with the heads of the screws engaging the top surface of the plate 48.

The rigid support 18 maintains the antenna a fixed distance from the skin of a patient being treated for optimum power application. If the distance is too great then the applicator becomes 20 excessively bulky and power resolution is compromised due to the electromagnetic fields having excessive overlap. The geometry of the spiral is dictated by the frequency of operation. For an antenna operating at 915 MHz, the diameter of the outer conductor should be approximately 3.5 cm, while the spiral antenna operating at 433 MHz should be approximately 8.5 cm in diameter. In one embodiment with the antennas being energized by a signal at 915 MHz, the cube is 3 ½ centimeters on a side with a center to center antenna spacing of 3.8 centimeter. This permits if required, a uniformly flat electromagnetic field, though varying the power rationing to each antenna can customize the spatial power distribution to treat non-homogeneous tissue. If the antennas are spaced further apart power deposition gaps appear between the antennas and insufficient heating results.

In operation, temperature sensors will be positioned on the patient's skin surface to monitor the temperature at the surface of the patent. Additional probes will be placed subcutaneously to monitor tissue at depth. The fluid circulated through the bolus can be temperature regulated to control the skin temperature of the treated region.

A flexible microwave blanket in accordance with the invention facilitates the hyperthermia treatment of superficially located tumors on complex surface areas of a patient such as around the neck, chest, and extremities. The rigid supports maintain the proper spacing and alignment of the antennas with the surface of the patient while the use of individual supports for the antennas facilitates the flexing thereof. The transparent housing and support structure allow a technician to visually inspect the array as it is positioned on a patient for treatment.

While the invention has been described with reference to a specific embodiment, the description is illustrative of the invention and is not to be construed as limiting the invention. For example, many types of antennas can be employed such as subminiature wave guides and microstrip patch antennas. Thus, various modifications and applications may occur to those skilled in the art without departing from the true spirit and scope of the invention as defined by the appended claims.

I claim:

1. A flexible two dimensional microwave array for hyperthermia of superficially located tumors on complex two dimensional body contours comprising
    a flexible, fluid permeable base member,
    a plurality of rigid platforms positioned on said flexible base member,
    a plurality of antennas with each antenna mounted on a platform and spaced from said flexible base member,
    means flexibly attaching each platform to adjacent platforms for maintaining said platforms in an array,
    means for encasing said platforms and said flexible fluid permeable base member in a fluid environment, and
    means for energizing each antenna.

2. The flexible microwave array as defined by claim 1 and further including means for applying fluid to said fluid environment.

3. The flexible microwave array as defined by claim 2 and further including means for circulating a fluid in said fluid environment.

4. The flexible microwave array as defined by claim 1 wherein each platform comprises a plurality of rigid sheets arranged as a cube, said antennas being mounted on said cubes.

5. The flexible microwave array as defined by claim 4 wherein each antenna comprises a printed circuit board in which an electromagnetically radiating conductive pattern is defined on one side and aground plane is provided on the opposing side.

6. The flexible microwave array as defined by claim 5 wherein each antenna is affixed to an inside surface of one sheet of a cube, said means for energizing each antenna comprising a coaxial connector including a flange which is mounted on said ground plane of said printed circuit board.

7. The flexible microwave array as defined by claim 6 and further including holes through corners of said cube opposite from said printed circuit board to facilitate the attachment of corners of adjacent cubes.

8. The flexible microwave array as defined by claim 7 wherein said means for encasing said platforms and said flexible base member in a fluid environment comprises sheet vinyl, and further including means for providing a fluid tight seal of said sheet vinyl on a top surface of each cube.

9. The flexible microwave array as defined by claim 8 wherein said means for providing a fluid tight seal comprises a plate, means for fastening said plate to said coaxial connector, and an o-ring provided between said plate and the top surface of each cube for preventing fluid leaks.

10. A flexible microwave array for hyperthermia of superficially located tumors comprising
a flexible base member,
a plurality of platforms positioned on said flexible base member, each platform comprising a plurality of rigid sheets arranged as a cube,
a plurality of antennas with each antenna mounted on a cube and spaced from said flexible base member,
means flexibly attaching each platform to adjacent platforms for maintaining said platforms in an array,
means for encasing said platforms and said flexible base member in a fluid environment, and
means for energizing each antenna.

11. The flexible microwave array as defined by claim 10 wherein each antenna comprises a printed circuit board in which an electromagnetically radiating conductive pattern is defined on one side and a ground plane is provided on the opposing side.

12. The flexible microwave array as defined by claim 11 wherein each antenna is affixed to an inside surface of one sheet of a cube, said means for energizing each antenna comprising a coaxial connector including a flange which is mounted on said ground plane of said printed circuit board.

13. The flexible microwave array as defined by claim 12 and further including holes through corners of said cube opposite from said printed circuit board to facilitate the attachment of corners of adjacent cubes.

14. The flexible microwave array as defined by claim 13 wherein said means for encasing said platforms and said flexible base member in a fluid environment comprises sheet vinyl, and further including means for providing a fluid tight seal of said sheet vinyl on a top surface of each cube.

15. The flexible microwave array as defined by claim 14 wherein said means for providing a fluid tight seal comprises a plate, means for fastening said plate to said coaxial connector, and an o-ring provided between said plate and the top surface of each cube for preventing fluid leaks.

* * * * *